United States Patent
Will et al.

(10) Patent No.: US 10,261,029 B2
(45) Date of Patent: Apr. 16, 2019

(54) CONTAINER INSPECTION DEVICE AND CONTAINER INSPECTION METHOD FOR INSPECTING CONTAINERS

(71) Applicant: Krones AG, Neutraubling (DE)

(72) Inventors: Christof Will, Obertraubling (DE); Anton Niedermeier, Offenstetten (DE); Karl Aichinger, Metten (DE); Reinhard Klinger, Bernhardswald (DE); Stefan Piana, Koefering (DE)

(73) Assignee: Krones AG, Neutraubling (DE)

( * ) Notice: Subject to any disclaimer, the term of this patent is extended or adjusted under 35 U.S.C. 154(b) by 0 days.

(21) Appl. No.: 15/567,511

(22) PCT Filed: Feb. 8, 2016

(86) PCT No.: PCT/EP2016/052635
§ 371 (c)(1),
(2) Date: Oct. 18, 2017

(87) PCT Pub. No.: WO2016/169667
PCT Pub. Date: Oct. 27, 2016

(65) Prior Publication Data
US 2018/0136142 A1 May 17, 2018

(30) Foreign Application Priority Data

Apr. 20, 2015 (DE) .................. 10 2015 106 013

(51) Int. Cl.
*G01N 21/90* (2006.01)
*G01N 21/88* (2006.01)
(Continued)

(52) U.S. Cl.
CPC ......... *G01N 21/90* (2013.01); *G01N 21/8806* (2013.01); *G01N 21/9009* (2013.01);
(Continued)

(58) Field of Classification Search
CPC ............... G01N 21/90; G01N 21/9009; G01N 21/8806; G01N 2201/0621;
(Continued)

(56) References Cited

U.S. PATENT DOCUMENTS

| 4,668,983 A | 5/1987 | Werson |
|---|---|---|
| 2001/0028227 A1 | 10/2001 | Lys et al. |
| 2003/0035103 A1 | 2/2003 | Werzinger et al. |
| 2005/0174473 A1 | 8/2005 | Morgan et al. |
| 2009/0033761 A1 | 2/2009 | Cetrulo et al. |

(Continued)

FOREIGN PATENT DOCUMENTS

| DE | 10017126 C1 | 6/2001 |
|---|---|---|
| DE | 102012104223 A1 | 9/2013 |
| DE | 102013106894 A1 | 1/2015 |

OTHER PUBLICATIONS

International Preliminary Report on Patentability and Written Opinion of the International Searching Authority dated Oct. 24, 2017 for corresponding International Application No. PCT/EP2016/052635.
(Continued)

*Primary Examiner* — Michael P Stafira
(74) *Attorney, Agent, or Firm* — Walter | Haverfield LLP; Sean F. Mellino; D. Peter Hochberg (57) ABSTRACT

A container inspection device and a container inspection method for inspecting containers are provided. The container inspection device comprises at least one light fixture for illuminating containers at a predetermined inspection instant of time for inspecting the containers, and an electrical line for connecting the at least one light fixture to an electrical energy supply and to a bus system, so that the electrical line serves both to supply the at least one light fixture with electrical energy and to connect with a real time data network.

12 Claims, 2 Drawing Sheets

(51) Int. Cl.
   *H05B 37/02* (2006.01)
   *H05B 33/08* (2006.01)
(52) U.S. Cl.
   CPC ............ *G01N 2021/8835* (2013.01); *G01N 2021/8838* (2013.01); *G01N 2201/0621* (2013.01); *G01N 2201/0695* (2013.01); *H05B 33/086* (2013.01); *H05B 33/0806* (2013.01); *H05B 37/0254* (2013.01)
(58) Field of Classification Search
   CPC ... G01N 2021/8835; G01N 2021/8838; G01N 21/9018; G01N 2201/0695; G01N 21/251; G01N 21/8851; G01N 21/9054; G01N 21/952; G01N 2201/062
   See application file for complete search history.

(56) References Cited

U.S. PATENT DOCUMENTS

| | | |
|---|---|---|
| 2010/0152889 A1 | 6/2010 | Langosch et al. |
| 2012/0113248 A1 | 5/2012 | Fiegler |
| 2012/0176735 A1 | 7/2012 | Davis |
| 2013/0083330 A1 | 4/2013 | Piana et al. |

OTHER PUBLICATIONS

Perry West, "High speed, real-time machine vision", Automated Vision Systems, Inc., CyberOptics—Imagenation, Retrieved from the Internet: URL:http://www.imagenation.com/pdf/highspeed.pdf.
International Search Report from the European Patent Office for corresponding International Application No. PCT/EP2016/052635 dated May 13, 2016.

CONTAINER INSPECTION DEVICE AND CONTAINER INSPECTION METHOD FOR INSPECTING CONTAINERS

CROSS REFERENCE TO RELATED APPLICATIONS

This application is a 371 National Stage application of International Application No. PCT/EP2016/052635 filed on Feb. 8, 2016, which claims foreign priority to German (DE) Application Serial No. 10 2015 106 013.2 filed on Apr. 20, 2015, the contents of which are incorporated herein by reference in its entireties.

BACKGROUND OF THE INVENTION

Field of the Invention

The present invention relates to a container inspection device and a container inspection method for inspecting containers or its secondary packaging units logically corresponding thereto like beverage crates and bundles or pallets. The container inspection device and the container inspection method may be employed in a container treatment plant, for example, in which the containers are inspected for faults, defects, etc.

Description of the Prior Art

DE 100 17 126 C1 shows a method and a device for optically examining transparent containers. The device for performing the method comprises a LED lighting screen having a plurality LEDs which can be activated individually or in groups. The LED lighting screen is positioned adjacent to a stream formed from a row of transparent containers positioned one after the other, a container stream. When the containers are illuminated by the LED lighting screen, a picture or image of the container can be taken to perform the optical examination of the containers.

An inspection device comprises, thus, an illumination, an optical recording unit and an image evaluating unit. The recording unit and the image evaluating unit may be realized in the same apparatus, like for example in so-called vision-sensors or intelligent cameras, but may also be implemented separately, like for example in a camera and a separate image evaluating unit.

For the illumination of the inspection device, different kinds of technical light fixtures are used in general in the field of inspection. The illumination can be implemented as permanent light or switched light or flashed light. Illuminating with permanent light is understood in this context as comprising a luminous time $T_{ON}$ of 1 second to $\infty$. When illuminating with switched light, the luminous time $T_{ON}$ has a value of approximately 150 µs up to approximately 2 s. When illuminating with flashed light, the luminous time $T_{ON}$ has a value of approximately 1 µs to 400 µs. The transitions are fluent. In the other time, that is the non-luminous time, the illumination is switched off. This time in which it is not illuminated is referenced as switched-off time $T_{OFF}$.

The inspection of containers, in particular the inspection of containers during the movement in container treatment plants for filling containers, is preferably implemented by flashed light. This is at the same time the most intricate illumination. In case the inspection task allows it, also a switched illumination or a permanent light may be employed. Flashed or switched illuminations can comprise an own energy storage to provide an energy amount which is big enough for the duration of the luminous time $T_{ON}$. In the following, flash illuminations are mentioned only, however, the explanations are valid for switched illuminations in the same way.

The initiating of an illumination is effected by a trigger signal which releases a predefined flash duration or is controlled by the signal length.

As a result, the illumination needs at least the following contacts for the energy supply, a flashed or switched illumination, and additionally a trigger-signal or a switch-on-signal ($T_{ON}$-signal) for initiating the flashed or switched illumination.

In the evaluating unit is used a shutter for the recording unit which may be implemented as a 1D-, 2D- or 3D-camera, wherein the shutter is open for a predetermined shutter time $T_S$ and releases a recording sensor.

Only the time intersection of the shutter time $T_S$ and the illuminating time $T_{ON}$ actually acts on the recording sensor and generates an image with the effective illuminating time $T_S$. The intensity of the resulting image is the integral of the light intensity in the recording sensor over the effective illuminating time $T_B$. Images of the same intensity can be achieved only, if the intensity of the illumination and the effective exposure time $T_B$ are constant.

In the technical implementation, either the luminous time $T_{ON}$ is set so that the shutter time $T_S$ is always inside the luminous time $T_{ON}$ or that the luminous time $T_{ON}$ is always inside the shutter time $T_S$. However, the luminous time $T_{ON}$ should not be lengthened arbitrarily, since the advantages of the luminous time $T_{ON}$ which is to be actually chosen, are lost in this case. In the case of the other way round, also the shutter time $T_S$ should not be lengthened arbitrarily, since in this case the recording sensor is sensitive to extraneous light, like environment light or light flashes, from other inspection units and can confuse the subsequent evaluation.

To avoid the mentioned disadvantages, the illumination has to be synchronized with the recording unit. In the prior art, the synchronization is achieved by a common trigger line or the recording unit controls the illumination by a digital output. It is further possible that the illumination controls the recording unit.

A synchronization of a clock of the recording unit and a clock of the illumination can be made for example by a computer network on which runs an established time protocol like SNTP or NTP. However, a computer network cannot guarantee, that a communication packet reaches the recording unit and the illumination as the parties or rather nodes of the synchronization within a predefined time. The predefined time derives itself for example from the field of view of the recording unit as well as the reaction time for recording after the detection of the container. The smaller the field of view, the shorter is the path between the detection of the container and the location of the record. The time for a transport of the container along the path is calculated from the transport velocity of the container treatment plant, which accounts in a stretch blow molding machine up to 8 m/s. A rotary encoder signal is relevant for the reaction time. It is examined with the rotary encoder signal approximately every 100 µs to 10 ms, typically every 0.2 to 5 ms, whether the container has actually passed the path between the detection of the container and the location of the recording. The container detection signal and the rotary encoder signal are stimuli for the decision, when a record shall be initiated by the recording unit. Because of the short reaction time resulting for the mentioned conditions for a container treatment plant and therewith the predetermined time, the computer network is not applicable for the timely, synchronized initiation of the exposure and flash time and therewith for the required synchronization.

A further disadvantage of hitherto solutions in a container inspection device for a container treatment plant is given by the intricate cabling. For a container treatment plant, the illumination has to be reconfigured frequently since the lamp color has to be adapted to the container material, luminous segments have to be adapted to the container geometry, etc. In these cases, a supply cable with trigger signal and further lines have to be connected to the illumination.

As regards the trigger line, there is also the problem that a line which is installed unfavorable can couple in disturbances and can uncontrollably initiate a flash illumination. Wrongly, uncontrollably initiated triggers use energy of the energy storage of the illumination inadvertently. If the energy storage is not loaded sufficiently, a necessary flash cannot be performed with the complete brightness. As a result, the brightness fluctuates in the recorded image, in the worst case, the image is too dark. Therewith, the burden of the cabling increases, since power guiding (motor) lines are to be installed separately from the trigger line.

A further problem lies in that a plurality of fast output contacts are required as regards a container inspection device. Not only the stimuli have to be read in in a higher ranking system, but also the output contacts have to be provided. Therewith, the costs of the container treatment plant increase.

A further disadvantage lies in that the cabling topology has to be known in advance. Possible changes or additions require a change of the cabling plan. Example: recording unit A and B use the same illumination. The recording units A, B act independent from each other. The output contacts of both recording units A, B control the illumination. Diodes are used for decoupling. In case it is to be changed per worked product between a through-light-illumination C and incident illumination D, the synchronization between the cameras and the illuminations is very intricate. A solution may be additional AND-gates in the illumination path. However, the trigger possibilities have to be known also here a priori.

SUMMARY OF THE PRESENT INVENTION

Therefore, it is the object of the present invention to provide a container inspection device and a container inspection method for inspecting containers with which the above-mentioned problems can be solved. In particular, a container inspection device and a container inspection method for inspecting containers shall be provided which can realize that an inspection of containers reliably fulfills the required quality requirements and is nevertheless realizable with ease and low costs.

The object is solved by a container inspection device for inspecting containers according to claim 1. The container inspection device comprises at least one light fixture for illuminating containers at a predetermined inspection instant of time for inspecting the containers, and an electrical line for connecting the at least one light fixture to an electrical energy supply and a bus system, so that the electrical line serves both to supply the at least one light fixture with electrical energy and to connect with a real time data network.

With the container inspection device, the requirements to the real time capability for an inspection of the containers can be fulfilled with low cost and effectively.

A further advantage lies in that, the complexity of a cabling between the individual components of the container inspection device or rather the container treatment plant and in the electrical cabinet of the container inspection device is remarkably reduced, if the cabling is made only by one line or rather plug connection. The container inspection device comprises a one-line-solution for its light fixtures and peripheral devices. Altogether, there are remarkably less electrical lines to be installed in and for the container inspection device. Therefrom results a space reduction in the electrical cabinet, as well.

Thus, a bus connection of flash illuminations via one-line-solution is described with the bus system, such that only one line is to be led to the illumination or rather to the light fixtures. By the line are realized the energy supply, the real time data, like for example trigger, and possibly also the parameterization of the illumination. Thus, no separate trigger line is to be brought up to the light fixtures. A further advantage lies in that the way of transmitting real time data, i.e. the trigger signal, is very insensitive as regards electromagnetic radiation. Therewith, the cabling of the light fixtures or rather flash illuminations is remarkably simplified with simultaneous amelioration of the trigger reliability.

Therefrom results also the advantage of an easy expansion of the entire system by single components, since no hardware expansion of the central system is required for this, but a further bus member has to be looped into the combined bus and supply line. It is also advantageous here that plural light fixtures or lamps or also other correspondingly equipped apparatuses can be wired in a chain ("Daisy Chain") with ease.

A big advantage lies also therein that the cabling topology is independent from the trigger topology. This increases the flexibility of the entire system.

Moreover, it is an advantage that no control outputs at the recording unit or at a high-ranking location are required for the triggers of the illumination.

It is further advantageous that synchronization mechanisms between plural light fixtures or lamps can be implemented easily as a software function and no transverse cabling is required. Therewith, the suppression or delay of the flash of a second illumination or another, adjacent inspection system can be realized, during a first illumination is active. Therewith, disturbing light reflexes or scattered light, for example, can be avoided.

A further advantage arises in that an independent topology can be standardized and a fault in the implementation can occur neither in planning, manufacturing nor putting into service of a work order. The elimination of fault incidents reduces the burden and the system can thus be implemented with low cost.

Advantageous further developments of the container inspection device are mentioned in the dependent claims.

The bus system is advantageously further configured for supplying a trigger signal to the at least one light fixture, to trigger the illumination of the containers at the predetermined inspection instant of time for inspecting the containers. Therewith, the cabling of the container inspection device is configured much less intricate as well as more space saving and more cost-effective.

Herein, the trigger signal can be configured for triggering the at least one light fixture by oversampling the bus system in the one-digit microsecond range.

It is conceivable that the electrical line is a data cable from which at least one lead pair is provided for connecting to the electrical energy supply and at least one lead pair is provided for connecting to the bus system.

Possibly, the at least one light fixture is a LED-flash light fixture which comprises an energy buffer for intermediate storage of the electrical energy supplied by the electrical energy supply, and wherein the energy buffer is configured such that the LED flash lamp can consume for a short time from the energy buffer an energy amount which is higher than the energy provided by the electrical energy supply in the time of the consumption. The buffer may be implemented as a condenser or an accumulator, for instance.

Herein, the energy buffer may be configured such that at least two light fixtures can flash simultaneously at least for a predetermined time in the predetermined inspection clock for illuminating the containers, and/or the container inspection device can be configured for controlling the LED-flash lamp such that for the same container in a container stream of a container treatment plant can be switched on different areas of the LED-flash light for inspecting a container.

Herein, the color and/or brightness of the at least one light fixture can be controllable, in particular during an illumination of a container.

The above-described container inspection device can be part of a container treatment plant for treating of containers.

The object is further solved by a container inspection method for inspecting containers according to claim 9. The container inspection method comprises the steps of: supplying, by an electrical line, at least one light fixture from an electrical energy supply with electrical energy, transmitting data, with the electrical line, via a bus system, such that the electrical line both supplies the at least one light fixture with electrical energy and connects to a real time data network, and illuminating containers at a predetermined inspection instant of time for inspecting the containers with the at least one light fixture or in a predetermined inspection clock for triggering via the real time capable bus line.

The container inspection method achieves the same advantages as they are mentioned in respect of the container inspection device.

Further possible implementations of the invention comprise also combinations of features or styles described above or in the following with reference to the embodiments, even if they are not explicitly mentioned. Herein, the person skilled in the art will also add single aspects as improvements or additions to the respective basic form of the invention.

BRIEF DESCRIPTION OF THE DRAWINGS

In the following, the invention is described in more detail by means of embodiments and with reference to the appended drawing Figures, wherein.

DETAILED DESCRIPTION OF THE PRESENT INVENTION

In the figures, the same or functionally same elements are provided with the same reference signs unless given otherwise.

Figure 1:
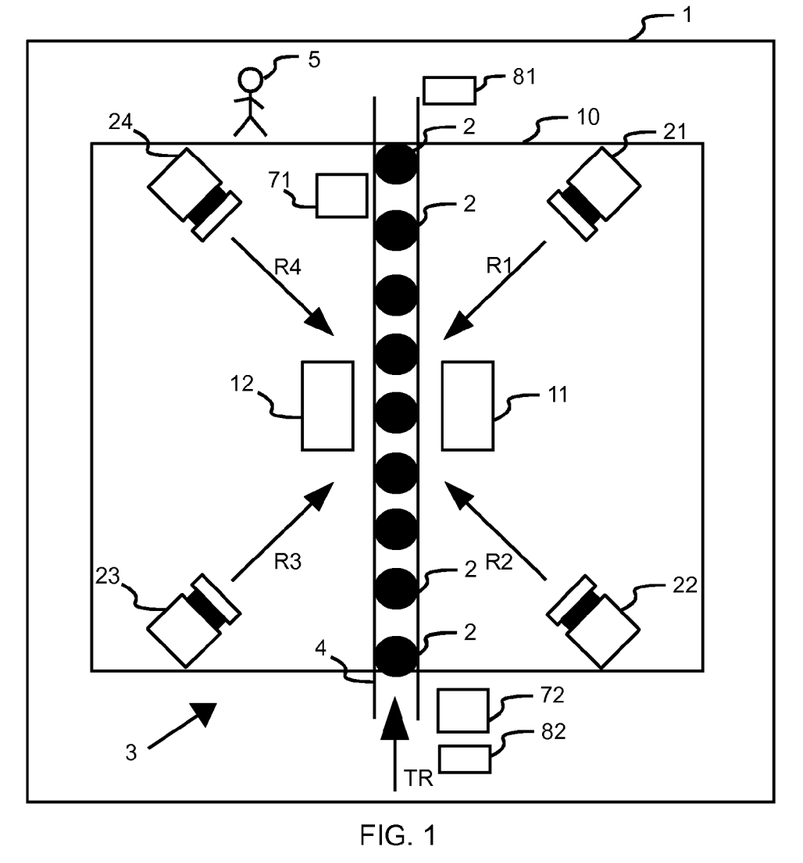
FIG. 1 shows a block diagram for illustrating a machine comprising a container inspection device according to a first embodiment.

FIG. 1 shows very schematically a machine 1, which can be, for example a container treatment plant, in particular an empty bottle inspection machine, a full bottle inspection machine, a label control unit, a tap inspection machine, a preform inspection machine, a filling height control machine, a stretch blow molding machine, a filling machine, a machine for treating glass containers, etc., a packing plant, a crate inspection plant, etc. Even if the machine 1 is described in the following partly using the example of a container treatment plant, the machine 1 is not limited thereto.

In the machine 1, containers 2, in particular transparent plastic bottles, glass bottles, metal cans, preforms, full, empty, closed, unclosed, labeled, not labeled, etc., are produced and/or treated. It is meant therewith, that the inspection systems described in the following can be positioned upstream and/or downstream of each treatment step in the container treatment plant. In the machine 1, secondary packaging units, like beverage crates and bundles or pallets, can be inspected, too, which are logically assigned to the containers 2.

In FIG. 1, not all of the containers 2 are provided with reference signs for the sake of simplicity. The containers 2 are moved, by the use of a transport unit 4 through a container inspection device 10 in the direction of an arrow TR, in a container stream 3 in which the containers 2 are positioned each individually in a row one after another. Herein, the containers 2 are moved to pass by light fixtures 11, 12 and recoding units 21. The machine 1 is, for example, operated or only watched by a person 5. Light barriers 71, 72 and/or rotary encoders 81, 82 can detect statuses of the containers 2 at the transport unit 4 or only a movement, in particular rotation, of the transport unit 4 without containers 2. The light barriers 71, 72 and/or rotary encoders 81, 82 can be employed to detect the path of the containers 2 and therewith to determine the velocity of the container stream 3. The light barriers 71, 72 and/or rotary encoders 81, 82 are positioned peripheral, in particular at the intake and/or outlet of the containers 2 in/out of the container inspection device 10.

As regards the container inspection device 10 of FIG. 1, the light fixture 11 is positioned between the recording units 21, 22 on the one side of the container stream 3. The light fixture 12 is positioned between the recoding units 23, 24 on the other side of the container stream 3. In this way, the containers 2 can be illuminated from two different sides. The recording units 23, 24 are positioned herein such that they can record images of each of the containers 2 from, for example, the four directions R1, R2, R4, R5, which are depicted in FIG. 1 by an arrow. If necessary, the recording units 21, 22, 23, 34 can be positioned differently, too, so that images can be recorded in an angle from the top above the light fixture 11 or in an angle from the bottom beneath the light fixture 12 and/or images are recorded from different heights of the container 2, for example, etc.

Figure 2:
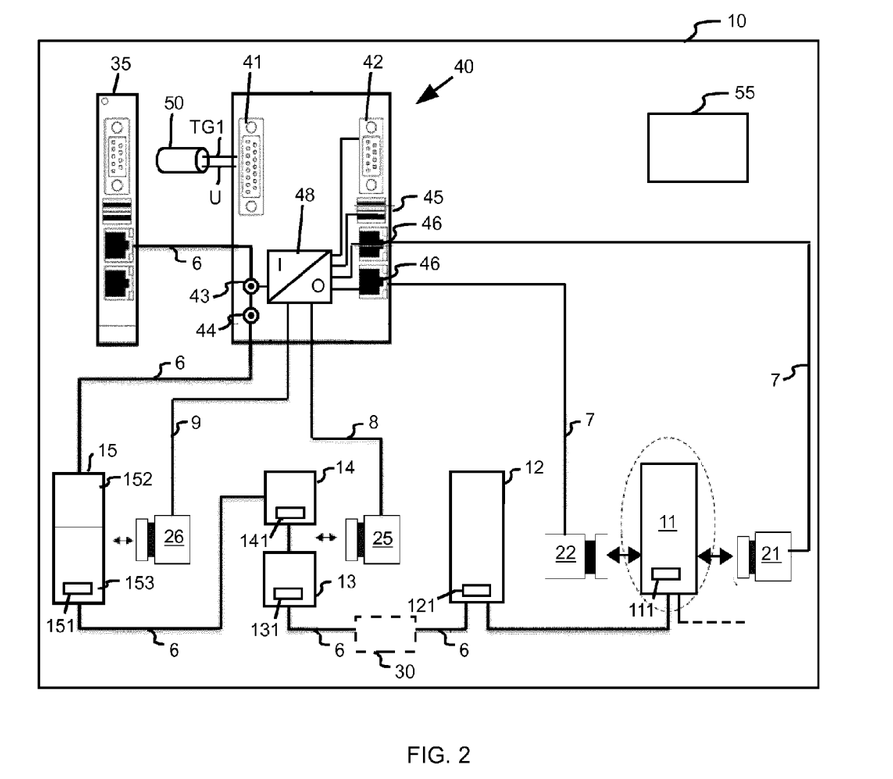
FIG. 2 shows a block diagram for illustrating the electrical cabling of the container inspection device according to the first embodiment.

One or both light fixtures 11, 12 illuminate the containers 2 because of a driving of the detection system such that one or more of the recording units 21 to 24 can optically detect the containers 2, wherein the driving is illustrated in FIG. 2. The recording units 21 to 24 can record, for example, images which can be evaluated for identifying faults, defects, etc. of the containers 2. The recording units 21 to 24 can be cameras.

The selection of the kind of the light fixtures 11, 12 is dependent on several general requirements, like for example on the price, energy consumption (=heat development) and the mutual impact of further inspection devices. In the selection of the illuminant (lamp), all of the kinds of electrical illuminants are employed. Besides LED-lamps, also lamps like light bulbs, tungsten halogen lamps, fluorescent lamps, high pressure discharge lamps and low pressure discharge lamps can be used. The wave length of the illuminants includes the range of radiation having a frequency in the Tera-Hertz-range up to the range of the wavelength of X-rays.

FIG. 2 shows a specific configuration of the container inspection device 10 in more detail. In the machine 1 is provided a bus system 6 to which are connected many of the components of the machine 1. Additionally, connection lines 7, 8, 9 are provided.

In the bus system 6, data can be transmitted via an electrical line in real time, for example with the Profinet standard (Profinet=Process Field Network) or the Ethernet POWERLINK-Standard, or according to the EtherCAT-Standard (Ethernet for Control Automation Technology) according to the IEC 61158, etc. The bus system 6 is in particular an Ethernet real time field bus. The bus system 6 provides a real time data network.

Via the point-to-point connection (point-to-point: in the classical meaning—that is the connection path totally without intermediate station) 7, 8 or 9, industry cameras can be connected as recording units 21 to 26 to existing data networks by the use of the Gigabit Ethernet standard. In FIG. 2, the recording units 23, 24 are not shown. The connection line 7 can be realized in particular for the GigEVision® standard. The connection line 8 can connect a recording unit 25 via a USB interface to an image recording system 40. Likewise, with the connection line 9, a connection via alternative vision protocols, like for example FireWire or CoaXPress would be possible.

In FIG. 2, the container inspection device 10 comprises the first light fixture 11 having an energy buffer 111, a second light fixture 12 having an energy buffer 121, a third lamp 13 having an energy buffer 131, a fourth lamp 14 having an energy buffer 141, a fifth lamp 15 having an energy buffer 151 and a first and second luminous field 152, 153, the first and second recording unit 21, 22, a fifth recording unit 25 and a sixth recording unit 26, wherein the recording units 21, 22, 25, 26 form a detection system and/or can be implemented in general as optical detection units, an optional power-injector or rather an electrical energy supply 30, a bus system controller 35, an image recording system 40 having a connecting module 41 and to which is connected an electrical line 50, and a general user interface 55. Also the signals of the light barriers 71, 72 and/or rotary encoders 81, 82 can be passed on to the bus controller 35, even if this is not depicted in FIG. 2.

Further, the light fixture 15 can comprise more than two luminous fields 152, 153 which are drivable separately from each other and can thus be illuminated separately from each other. As regards the second light fixture 14, an illumination can be controlled in respect of the color and/or brightness gradient.

The energy buffers 111, 121, 131, 141, 151 are designed such that the assigned light fixture 11 to 15 or rather flash light fixture may withdraw short-term an energy amount which is higher than the energy provided from the electrical energy supply in the time of the withdrawal or consumption. At least one light fixture 11 to 14 and/or one lamp 15 having two separate luminous fields 152, 153 can be supplied with the energy buffer 111 or the other energy buffers of the light fixtures 12 to 15 with energy for flashing at least temporary simultaneously and/or shortly one after the other and/or with different duration and/or different electric current.

Therewith, the light fixtures 11 to 15 form a flash apparatus that provides very much light for a very short time or in a pulsed manner. The light pulse does not last very long, in full power mostly only few thousandth seconds, as described before in the introductory portion of the description.

Instead of supplying a voltage U by the energy supply unit provided in the connection module 41, the optional power-injector or rather electrical energy supply 30 can take over or supplement the current supply of the light fixtures 11 to 15 and be looped into the real time bus system 6 at an arbitrary position. In case many light fixtures 11 to 15 or other consumers are connected to the line for the real time bus system 6, the inlet for the electrical energy supply can be carried out at several positions.

In FIG. 2, the simplified depicted image recording system 40 comprises a connection module 41. The connection module 41 serves to connect the electrical line 50 via which an electrical energy supply with the voltage U and the trigger signal TG1 are led on different leads or lead pairs. The image recording system 40 further comprises contacts 43, 44 for connecting both the bus system controller 35 and the line of the bus system 6, for example each via a data contact plug, like a RJ-45-plug. In addition, the image recording system 40 with its contacts 42, 45 and 46 shows various connection possibilities for different camera interfaces, like USB Vision Kamera Link, CoaXPress, GigEVision or furthers, by the use of the contact lines 7, 8 and 9. The real time bus system 6 and the contact lines 7, 8, 9 are clearly separated via an I/O-Modul or rather in/output module 48 from each other.

The general user interface 55 can be implemented as a personal computer (PC) and can also be referred to as GUI-PC. With the general user interface 55, the person 5 can operate and watch the container inspection device 10.

In the image recording system 40 of FIG. 2, a real time bus, for example EtherCat, is employed, in conjunction with the electrical supply of the illumination in a cable of the bus system 6, for triggering the illumination with at least one of the light fixtures 11 to 15. In case the illumination has to be configured additionally, this can be done with the same real time bus.

The electrical line for the bus system 6 leads, thus, both the energy supply for an illumination with the light fixtures 11 to 15 and the communication of the real time bus to the light fixtures 11 to 15. The electrical line for the bus system 6 includes at least one or more leads or lead pairs. The electrical energy supply can therewith use the same leads like the communication or a part of these leads. It can also be led via separate leads in the line. The electrical line for the bus system 6 can be implemented as data cable from which at least one lead pair is provided for connecting to the electrical energy supply and at least one lead pair for connecting to the bus system.

The light fixtures 11 to 15 get the electrical line for the bus system 6 as a connection line or cable, wherein further lines or cables are not necessary. However, the light fixtures 11 to 15 can have each a further contact. This contact connects via a second line for the bus system 6 a further lamp of the light fixtures 11 to 15, etc., so that some kind of a chain is produced.

The real time bus system 6 is not only reserved for the light fixtures 11 to 15. At the real time bus system 6, measuring units may be included as nodes which deliver the stimuli for the inspection of containers 2. Thereto belong different sensors, like, for example, the light barriers 71, 72, IR sensors, HF brine sensors, the rotary encoders 81, 82, distance sensors, metal sensors, color sensors, etc. The sensors can be connected directly to the real time bus system 6 via an own interface, or via an input/output apparatus to the real time bus system 6. It is possible that also these sensors or input/output apparatuses are fed by the use of the energy supply existent in the line of the real time bus system 6.

At least one recording unit 21, 22, 25, 26 of the image recording system 40 is connected by a real time interface to the same real time bus system 6. However, there is existent a clear separation of the real time bus system 6 to the connection line 7, as shown in FIG. 2 via the input/output module 48 and as mentioned already before. An image recording system 40 can support a recording unit 21, 22, 25, 26 or plural independent recording units 21, 22, 25, 26. The interface between the recording unit 21, 22, 25, 26 and the image recording system 40 can be configured differently. Typical interfaces between the image recording systems 40 and recording units 21, 22, 25, 26 can be an open standard, like GigE Vision, USB, Camera Link, or others, but may also be a proprietary interface. The image recording system 40 may be an intelligent camera with real time bus interface. However, because of the configuration described before and in the following, it is observed strictly inside the image recording system that the bus system 6 and the network in conjunction with the connection line 7 are separated from each other, that is, are not similar or the same.

The real time bus system 6 makes sure that data are sent and received in a finite time and short reaction time or delay time $T_D$. The real time bus system 6 offers the capability that plural or all of the nodes connected to the real time bus system 6 work with chronological synchronism, similar to a computer network. The data are sent in a so-called frame or a message.

It is secured in the real time bus system 6 that the frame is cyclically exchanged between all nodes, like light fixtures 11 to 15, sensors, etc. The cycle time for sending a frame in the real time bus system 6 can have a value from less than a millisecond to up to plural milliseconds. The values of 0.5 ms to 10 ms are typical for the inspection technique, ideal are 1 to 2 ms. The real time bus system 6 can synchronize the nodes to up to a few nanoseconds. In the practical realization, apparatuses, like the nodes of the real time bus system 6, in particular the light fixtures 11 to 15 and the recording units 21, 22, 25, 26 can execute actions which are synchronous in time to each other in the single-digit μs-range. Therewith, the action can be performed extremely synchronous via the real time bus system 6 and distributed to plural apparatuses, like the nodes of the real time bus system 6, in particular the light fixtures 11 to 15 and the recording units 21, 22, 25, 26, within a very short reaction time between stimuli and the derived action. An action in the sense of the present description is the synchronous execution of the exposure with the respective recording unit 21, 22, 25, 26 and the lamp flash of the light fixtures 11 to 15.

The apparatuses are 1000 times more synchronous to each other than the cycle time since the synchronization in respect of the apparatuses is in the μs-range instead of ms. Now, the execution time point in at least two different devices is to be distinguished between the reaction time, between stimuli and action and the synchronization. The reaction time is the time which elapses until at least one action from input stimuli reaches the executing apparatus. The real time bus system 6 used in the container inspection device 10 offers both.

The bus system 6 of the container inspection device 10 is configured such that a trigger signal TG1, TG2 can trigger arbitrary lamps of the light fixtures 11 to 15 or arbitrary luminous fields of the luminous fields 152, 153 of the light fixture 11 or rather arbitrary combinations of the recording units 21 to 26 and flash or rather exposure time combinations. For example, the combination is conceivable, to trigger the recording unit 25 and simultaneously, to activate the light fixture 12, which is in particular a transmitted light lamp, for a time duration of 100 μs during an exposure time of 100 μs of the recording unit 25 and to let flash at the same time the lamp 13, which is in particular an incident light lamp, for a time duration of 50 μs.

Alternatively or additionally, it is possible to activate for a 100 μs recording with the recording unit 22 the light fixture 11 for a time duration of 50 μs and to activate then subsequently for further 50 μs the light fixture 12 or a luminous field of the light fixture 12 which is not depicted.

A further configuration possibility of the container inspection device 10 is that via the μs-exact control of image recording by one of the recording units 21 to 26 the brightness of the recorded image can be achieved via the flash length and/or energy of one of the light fixtures 11 to 15 or one luminous field of the luminous fields 152, 153 of the lamp 15.

A further configuration possibility lies in that different luminous fields 152, 153 of the lamp 15 are activated at different instants of time during a recording with the recording unit 26. This is necessary, for example, when patterns and/or contrast edges of a container 2 or its label or closure, etc. have to be generated.

A further configuration possibility is the targeted switching-on of different color spectra via, for example, the light fixture 12, wherein here the switching-on of the red-green-blue-spectrum (RGB-spectrum) via a light emission diode (LED) can be mentioned likewise as the near IR-spectrum and/or the UV-spectrum. It goes without saying in this conjunction that all mixed colors can be generated herein, in particular also in the run-time of the flash procedure.

The bus system 6 is configured such that a change of the bus topology is possible, i.e. an addition or removal of a bus node in the operation of the container inspection device 10 ("hot-plug"). Moreover, the container inspection device 10 is modularly extendible. These capabilities are notably advantageous, since a standstill of the container treatment plant as machine 1 will be as short as possible in the grade change, therewith.

Due to the construction described before, the container inspection device 10 comprises a very sturdy construction both mechanically and thermally as well as in respect of the EMV-protection provisions.

Figure 3:
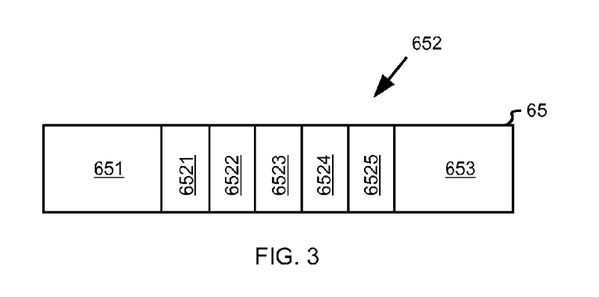
FIG. 3 shows a schematic view of a data frame which is transmitted in the bus system of the container inspection device according to the first embodiment.

FIG. 3 shows a frame 65 for a transmission of data in the bus system 6 of the container inspection device 10 according to a second embodiment. The container inspection device 10 and the corresponding machine 1 are implemented in many parts in the same way like described in respect of the first embodiment. Therefore, only the differences to the first embodiment are described in the following.

The frame 65 in FIG. 3 comprises a frame head 651, a data portion 652 and a frame end 652. The data portion comprises data blocks 6521 to 6525.

As mentioned above, the real time bus system 6 cyclically sends, at the end of the cycle time, the frame 65 to all nodes. In case the reaction time, cycle time is sufficient, in the sense of between shortest instant of time between stimuli and action, but the granularity of the cycle time in the application is not yet sufficient, a data block 6521 to 6525 in the data portion 652 can be interpreted as oversampling for a specific node. This is explained via the following example.

For example, a trigger TG1 should be initiated in 1.6 ms. The cycle time accounts for 1 ms. In a simple case, the trigger TG1 can be initiated in a millisecond or after two milliseconds. In case 5 values are used in the data portion 652, now, an oversampling can be performed. That is, each value represents an execution instant of time in a 0.2 ms raster. In the example, the information [0,0,0,1,0] in the data portion 652 in the data blocks 6521 to 6525 would signify the oversampling of the trigger instant of time. Therewith, it is possible to execute a trigger in 1.6 ms with a time resolution of 200 µs, although the cycle of the bus system 6 accounts for 1 ms in the example. Even if this example describes a fivefold oversampling, the oversampling in the data portion 652 may be decreased or increased.

It is not obligatory that the oversampling is the same for all of the nodes. In the same real time bus, nodes may be operated with a higher oversampling, others with no oversampling, and still further nodes with a lower oversampling.

According to a modification of the second embodiment, the oversampling is interpreted as a number instead of the above-described binary digitalization. Herewith, a granularity of 256 steps may be achieved with 8 binary places, for example. In the example, the granularity would then be approximately 3.9 µs.

Whether the oversampling is interpreted as a "time slice" (second embodiment) or a value or number (modification of the second embodiment), is only a question of the necessity. Both are possible. Both have merits. With the same storage allocation, the granularity may be increased or plural flashes may be initiated shortly one after the other with one of the light fixtures 11 to 15.

For example, five places are reserved in the data portion 652 as [0,0,0,0,0], wherein the cycle time accounts for 1 ms. Therewith, the granularity of $2^5=32$ subdivisions can be achieved with a resolution of 1 ms/32=31.25 µs. Alternatively, each of the 5 places may be interpreted as a time slice of 200 µs. Dependent on the inspection task, both interpretations are possible in the same real time bus system 6. The content [0,0,1,0,1] may signify 1) Initiating a flash in $(2^4*0+2^3*0+2^2*1+2^1*0+2^0*0)*31.25$ µs=5*31.25 µs=156.25 µs, if the data content is interpreted as a binary number. 2) Initiating two flashes at the instances of time 400 µs and 800 µs. Therewith, a flash can be initiated either highly granular. Or, flashes are initiated with the same illumination with the time-lag of 400 µs. These may be synchronized with two recording units 21, 22. The recording unit 21 "receives" the information [0,0,1,0,0] in the data portion 652 and records, thus, a recording or shot with the illumination of the light fixture 11 at the instant of time 400 µs. The recording unit 22 "receives" the information [0,0,0,0,1] in the data portion 652 and records, thus, a recording or shot with the same illumination at the point in time 800 µs. In practice, the information in the image recording system 40 is separated and fed into the appropriate connection lines 7 for the recording units 21, 22.

Apart from that, the container inspection device 10 according to the present embodiment is implemented in the same way as described with respect to the first embodiment.

All of the above-described implementations of the container inspection device 10 and the container inspection method can be used separately or in all possible combinations thereof. In particular, an arbitrary combination of the features of the first to third embodiments is possible. Moreover, in particular the following modifications are conceivable.

The elements shown in the figures are depicted schematically and can differ in the specific implementation from the forms shown in the figures provided that the above-described functions are ensured.

The container inspection device 10 can comprise also only one light fixture, for example the first light fixture 11 or two light fixtures. Alternatively, the container inspection device 10 can also comprise more than the shown five light fixtures.

Further, the container inspection device 10 can also comprise only one recording unit, for example the first recording unit 21. Alternatively, the container inspection device 10 can also comprise more than six recording units.

It is possible additionally or alternatively that different ranges of the light fixtures 11 to 15 in the form of a LED flash light fixture are switched on one after the other for the inspection of a container 2 for successive containers 2 in a container stream 3 of a container treatment plant.

In each of the embodiments, at least one of the light fixtures 11 to 15 can be driven such that the power P for one flash of the light fixture 11 to 15 continuously increases over the time. Furthermore, another lamp of the light fixtures 11 to 15 can be driven such that the power of the light fixture 11 to 15 continuously decreases over the time t. Herein, other variations are conceivable, too.

In each of the embodiments, the light fixtures 11 to 15 can be driven when illuminating the container stream 3 with the maximum power of the light fixture 11 to 15, in case one or more of the recording units 21 to 26 shall perform an optical detection or image recording.

Having described preferred embodiments of the invention, it will be apparent to those skilled in the art to which this invention relates, that modifications and amendments to various features and items can be effected and yet still come within the general concept of the invention. It is to be understood that all such modifications and amendments are intended to be included within the scope of the present invention.

What is claimed is:

1. A container inspection device for inspecting containers, the container inspection device comprising:
   at least one light fixture for illuminating containers at a predetermined inspection instant of time for inspecting the containers; and
   an electrical line for connecting the at least one light fixture to an electrical energy supply and to a bus system, so that the electrical line serves both to supply the at least one light fixture with electrical energy and to connect with a real time data network.

2. The container inspection device according to claim 1, wherein the bus system is further configured for supplying a trigger signal to the at least one light fixture, to trigger the illumination of the containers at the predetermined inspection instant of time for inspecting the containers.

3. The container inspection device according to claim 2, wherein the trigger signal is configured for triggering the at least one light fixture by oversampling the bus system in the one-digit microsecond range.

4. The container inspection device according to claim 1, wherein the electrical line is a data cable from which at least one lead pair is provided for connecting to the electrical energy supply and at least one lead pair is provided for connecting to the bus system.

5. The container inspection device according to claim 1, wherein the at least one light fixture is a LED-flash light fixture which comprises an energy buffer for intermediate storage of the electrical energy supplied by the electrical energy supply, and wherein the energy buffer is configured such that the LED flash lamp can consume an energy amount for a short time from the energy buffer which is higher than the energy provided by the electrical energy supply in the time of the consumption.

6. The container inspection device according to claim 5, wherein the energy buffer is configured such that at least two light fixtures can flash simultaneously at least for a predetermined time in the predetermined inspection clock for illuminating the containers.

7. The container inspection device according to claim 1, wherein a selected one of the group containing the color and brightness of the at least one light fixture is controllable, in particular during an illumination of a container.

8. A container treatment plant for treating containers, comprising a container inspection device for inspecting containers, the container inspection device comprising:
   at least one light fixture for illuminating containers at a predetermined inspection instant of time for inspecting the containers; and
   an electrical line for connecting the at least one light fixture to an electrical energy supply and to a bus system, so that the electrical line serves both to supply the at least one light fixture with electrical energy and to connect with a real time data network.

9. A container inspection method for inspecting containers, the method comprising the steps of:
   supplying, by an electrical line, at least one light fixture from an electrical energy supply with electrical energy;
   transmitting data, with the electrical line, via a bus system, such that the electrical line both supplies the at least one light fixture with electrical energy and connects to a real time data network; and
   illuminating containers at a predetermined inspection instant of time for inspecting the containers with the at least one light fixture.

10. The container inspection device according to claim 5, wherein the container inspection device is configured for controlling the LED-flash lamp such that for the same container in a container stream of a container treatment plant are switched on different areas of the LED-flash light for inspecting a container.

11. The container inspection device according to claim 1, wherein the container inspection device is configured such that a transport unit moves the containers through the container inspection device in a container stream in which the containers are positioned each individually in a row one after another; and
   wherein the container inspection device is configured such that the containers are moved to pass by the at least one light fixture so that the at least one light fixture illuminates the containers at a predetermined inspection instant of time for inspecting the containers one after another.

12. The container inspection method according to claim 9, wherein a transport unit moves the containers through the container inspection device in a container stream in which the containers are positioned each individually in a row one after another; and
   wherein the containers are moved to pass by the at least one light fixture so that the at least one light fixture illuminates the containers at a predetermined inspection instant of time for inspecting the containers one after another.

\* \* \* \* \*